(12) United States Patent
Conlon et al.

(10) Patent No.: US 6,632,675 B1
(45) Date of Patent: *Oct. 14, 2003

(54) MULTI-ANALYTE REFERENCE SOLUTIONS WITH STABLE PO₂ IN ZERO HEADSPACE CONTAINERS

(75) Inventors: Dennis R. Conlon, Attleboro, MA (US); Minna A. Rannikko, Worcester, MA (US); Kevin J. Sullivan, Medfield, MA (US); Robert B. Green, Hopkinton, MA (US)

(73) Assignee: Bayer Corporation, East Walpole, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/641,033

(22) Filed: Aug. 16, 2000

Related U.S. Application Data (60) Division of application No. 09/018,137, filed on Feb. 3, 1998, now Pat. No. 6,136,607, which is a continuation-in-part of application No. 08/740,410, filed on Oct. 29, 1996, now Pat. No. 5,780,302.
(60) Provisional application No. 60/006,742, filed on Nov. 2, 1995, now abandoned.

(51) Int. Cl.⁷ ............................................. G01N 31/00
(52) U.S. Cl. ..................... 436/11; 436/8; 436/9; 436/14; 436/15; 436/16; 436/68; 422/102; 422/103
(58) Field of Search .................. 436/8, 9, 11, 14, 436/15, 16, 66, 68; 422/99, 100, 102, 103

(56) References Cited

U.S. PATENT DOCUMENTS

| | | | |
|---|---|---|---|
| 3,681,255 A | 8/1972 | Wilfore | 436/11 X |
| 4,001,142 A | 1/1977 | Turner | 436/11 |
| 4,116,336 A | 9/1978 | Sorensen et al. | 436/11 X |
| 4,151,108 A | 4/1979 | Sorensen et al. | 436/11 |
| 4,163,734 A | 8/1979 | Sorensen et al. | 436/11 |
| 4,266,941 A | 5/1981 | Sullivan | 436/68 |
| 4,289,648 A | 9/1981 | Hoskins et al. | 422/83 X |
| 4,375,743 A | 3/1983 | Sullivan | 53/434 |
| 4,470,520 A | 9/1984 | Sullivan | 222/94 |
| 4,588,554 A | 5/1986 | Kaartinen et al. | 422/61 |
| 4,643,976 A | 2/1987 | Hoskins | 436/15 |
| 4,734,184 A | 3/1988 | Burleigh et al. | 204/409 |
| 4,753,888 A | 6/1988 | Chiang | 436/11 |
| 4,843,013 A | 6/1989 | Chiang | 436/11 |
| 4,945,062 A | 7/1990 | Chiang | 436/11 |
| 4,960,708 A | 10/1990 | Zowtiak et al. | 436/11 |
| 5,013,666 A | 5/1991 | Chiang | 436/11 |
| 5,023,186 A | 6/1991 | Herring | 436/11 |
| 5,230,427 A | 7/1993 | Betts et al. | 206/213.1 |
| 5,405,510 A | 4/1995 | Betts et al. | 204/153.1 |
| 5,421,981 A | 6/1995 | Leader et al. | 204/409 |
| 5,422,278 A | 6/1995 | Herring | 436/11 |
| 5,628,353 A | 5/1997 | Ruther | 141/330 |
| 5,637,505 A | 6/1997 | Li et al. | 436/8 |
| 5,780,302 A * | 7/1998 | Conlon et al. | 436/8 |
| 5,891,730 A | 4/1999 | Li et al. | 436/8 |

FOREIGN PATENT DOCUMENTS

| | | |
|---|---|---|
| EP | 0518191 | 12/1992 |
| EP | 0520443 | 12/1992 |
| EP | 0743523 | 11/1996 |
| GB | 2308444 | 6/1997 |
| WO | WO 93/21533 | 10/1993 |
| WO | WO 97/16309 | 5/1997 |
| WO | WO 97/44249 | 11/1997 |

OTHER PUBLICATIONS

Conlon et al. (1996), "Packaging Liquid Calibrators for pH, Blood Gases, & Electrolytes," *Clinical Chemistry* 42(6):S281, Abstract No. 771.

\* cited by examiner

*Primary Examiner*—Maureen M. Wallenhorst
(74) *Attorney, Agent, or Firm*—Reed & Eberle LLP; Dianne E. Reed; Louis L. Wu (57) ABSTRACT

Multi-analyte reference solutions having a stable partial pressure of oxygen (pO₂) in zero headspace packaging and methods for preparing such solutions are disclosed. The solutions have long shelf and use lives when stored at room temperature and are packaged in laminated foil containers having low or no oxygen reactivity. Access devices are also disclosed.

25 Claims, 5 Drawing Sheets

MULTI-ANALYTE REFERENCE SOLUTIONS WITH STABLE PO$_2$ IN ZERO HEADSPACE CONTAINERS

CROSS-REFERENCE TO RELATED APPLICATIONS

This application is a divisional of U.S. patent application Ser. No. 09/018,137, filed Feb. 3, 1998, now U.S. Pat. No. 6,136,607 issued on Oct. 24, 2000, which is a continuation-in-part of U.S. patent Ser. No. 08/740,410, filed Oct. 29, 1996, now U.S. Pat. No. 5,780,302 issued Jul. 14, 1998 and which claims priority to U.S. Provisional Application No. 60/006,742, filed Nov. 2, 1995, now abandoned. Priority from the above U.S. patents and application is claimed for this application under 35 U.S.C. § 119.

FIELD OF THE INVENTION

This invention relates primarily to the field of clinical reference solutions—quality control reagents and calibrators. More specifically it relates to methods of preparing multi-analyte reference solutions that have stable oxygen partial pressure (pO$_2$) in zero headspace containers, preferably in flexible foil laminate containers. The solutions are stable at room temperature and have long shelf and use lives.

BACKGROUND OF THE INVENTION

Clinical laboratories employ a variety of instrument systems for the analysis of patient samples. For example, pH/blood gas instruments measure blood pH, pCO$_2$ and pO$_2$. CO-Oximeter instruments typically measure the total hemoglobin concentration (tHb), and the hemoglobin fractions—oxyhemoglobin (O$_2$Hb), carboxyhemoglobin (COHb), methemoglobin (MetHb), reduced hemoglobin (HHb) and sulfhemoglobin (SHb)(collectively referred to as "CO-Ox fractions"). Ion selective electrode (ISE) instruments measure the content of blood electrolytes, such as, Na$^+$, Cl$^-$, Ca$^{++}$, K$^+$, Mg$^{++}$ and Li$^+$. Also, a variety of other parameters such as, metabolites, e.g., glucose, lactate, creatinine and urea, can be measured in clinical laboratories by related instrument systems.

Instrument systems currently available may combine the measurement of blood pH, gases, electrolytes, various metabolites, and CO-Ox fractions in one instrument for a comprehensive testing of the properties of blood. For example, all such analytes are measured by the Rapidlab™ 865 critical care diagnostics system from Chiron Diagnostics Corporation [Medfield, Mass. (USA)].

A calibrator is used to set the response level of the sensors. A control is used to verify the accuracy and reliability of such an instrumentation system.

A control is a solution having a known concentration of an analyte or analytes contained in the same, or a similar matrix in which the samples to be analyzed exist. The assay results from the control product are compared to the expected assay results to assure that the assay technique is performing as expected.

Commercial blood gas analysis systems have been available since the 1960s. The earliest reference-materials were gas mixtures in pressurized cylinders, and those materials are still commonly used. In the 1970s, the development of liquid reference solutions began, leading to products in which reagents have been equilibrated with precision gas mixtures and packaged in flexible containers with zero headspace, requiring either refrigeration to maintain stability or the resort to calculations to compensate for the expected pO$_2$ changes during storage.

Most quality control materials for such analyzers consist of tonometered aqueous solutions (a solution containing dissolved gases) in glass ampules. The typical gas headspace above the liquid in those ampules provides a reserve of oxygen against any potential oxygen-consuming reactions which may occur within the solution during the shelf life of the product.

In the absence of a gas headspace within their containers, reference solutions for oxygen determinations are particularly difficult to make and maintain stable. The inventors determined that the sources of said instability could be several.

First, the instability may be due to reactivity between the dissolved oxygen and the other components of the calibrator or quality control reagent. The other components might either react with the dissolved oxygen, reducing its concentration, or, alternatively, the other components may react with each other to generate oxygen, thus also changing the oxygen concentration. Second, the solution might be contaminated with microorganisms which, due to their metabolism, might change the oxygen content. Third, the oxygen might permeate through, or react with, the packaging material, also affecting the oxygen content of the reference material.

Reference materials that are manufactured for distribution in commerce must be made to withstand the various conditions encountered in the distribution chain and must be sufficiently stable to provide good performance within the time frame in which they are expected to be used by the customer, which is usually at least about six months, preferably for about nine months, and more preferably approximately 1 year for the typical calibrating or quality control solution distributed to commercial laboratories and hospitals. In addition, reference solutions, as with other reagents, should be packaged in containers which are easy to handle, convenient to use and which meet other design requirements of their intended usage. This is particularly true of reagents which are used in conjunction with various analytical instruments.

The users of instruments which determine the oxygen partial pressure of blood and other body fluids have a need for such reference materials and would benefit from liquid materials over the more conventional precision gas mixtures in cylinders with regulators. Liquid reference solutions are inherently less expensive, safer, and eajier to manipulate than high-pressure gas tanks.

Although reference solutions used in instruments measuring pO$_2$ have been made in the past, they have suffered from being unstable and having expensive, complicated, or unreliable means to access their contents. Some reference solutions, when used on analytical instruments, have extended their usefulness by allowing the instrument to calculate the expected oxygen level, said level being calculable from the age of the product, given the fact that the rate of decrease in oxygen level can be predicted based on historic performance [Conlon et al., *Clin. Chem.*, 42: 6—Abstract S281 (1996)]. Several developers have included inner layers of plastic materials selected because of their heat sealability (e.g., U.S. Pat. No. 5,405,510—Betts) or low gas permeability (U.S. Pat. No. 4,116,336—Sorensen) or gas tightness (U.S. Pat. No. 4,163,734—Sorensen). Some have disclosed that the inner layer should be inert, but have not provided enablement as to how to select such an inner layer (U.S. Pat. No. 4,643,976—Hoskins) and/or weren't capable of maintaining oxygen at a precise level appropriate for blood gas purposes.

Most blood gas/electrolyte/metabolite/CO-Oximetry/hematocrit quality controls (QCs) on the market today are provided in glass ampules which must be manually broken and manually presented to the analyzer. Rüther, H., U.S. Pat. No. 5,628,353 (issued May 13, 1997) describes an automated device which breaks open glass ampules by forcing a metal tube with thick walls and a small inner diameter, into the bottom of an ampule, and then aspirates the contents of the ampule into an analyzer. Such an automated ampule breaker is mechanically complex, requiring moving parts that are subject to wear and risk of failure, and could be subject to jamming and clogging from small bits of broken ampule glass.

In the 1980s, Kevin J. Sullivan disclosed an alternative to glass ampules—the first commercial product with a blood gas reagent in a flexible, zero headspace package [U.S. Pat. Nos. 4,266,941; 4,375,743; and 4,470,520]. Coated aluminum tubes were filled with 40–50 mL of blood gas QC solutions without any headspace. The tubes were enclosed in pressurized cans, to prevent outgassing and to supply a source of force to cause the QC solutions to flow into the sample path of a blood gas analyzer. One container of Sullivan's packaging design replaced about 30 glass ampules. Sullivan's packaging relieved the user of the task of opening many glass ampules and of the attendent risks of broken glass. The disadvantages of Sullivan's packaging included a need to refrigerate, a shelf life of less than a year, a menu of only three analytes, and the complexity and cost of a spring-loaded valve.

The instant invention not only overcomes the limitations of glass ampules, such as sensitivity of gas values to room temperature due to the headspace above the liquid, and complications resulting from the sharp edges which form upon breaking them open, or from the small, sharp glass pieces which can break off during ampule opening, but also overcomes the limitations of Sullivan's zero headspace packaging described above. The multi-analyte reference solutions with stable $pO_2$ of the instant invention are packaged in containers with zero headspace, preferably in flexible foil laminate containers, and are stable at room temperature for a shelf life of from about one to three years.

An additional shortcoming of storage devices for reference solutions for oxygen determinations (oxygen reference solutions) has been the opening or valve required to access the fluid for use, while maintaining the integrity of the fluid during storage. The materials available for valve construction and the need to breach the barrier layer to incorporate the valve may have compromised fluid stability. The access device disclosed herein for the preferred foil laminate containers used in the methods of the invention solves that problem. The simplicity of the one-piece valve should result in cost savings and greater reliability.

Further the multi-analyte reference solutions with stable $pO_2$ in zero headspace containers of this invention provide cost savings in that one such container can be the equivalent of a box of 30 or more ampules that are currently on the market. Further cost savings are provided in the consolidation of formulations in 5 level quality control (QC) reagents of this invention which are useful to control from about 5 to about 20 analytes. Providing a reduced number of formulations to control for pH/blood gas/electrolyte/metabolite/total hemoglobin (tHb)/hematocrit and CO-Oximetry analytes saves time on an analyzer system, allowing for more patient samples to be assayed, and consequently minimizes assay costs.

SUMMARY OF THE INVENTION

One object of this invention was to overcome the shortcomings of glass ampules as storage containers for QCs and calibrators used with whole blood analyzers, while allowing for automation of QC and calibrator delivery. In one aspect, the instant invention overcomes problems presented by glass ampules as storage containers for oxygen reference solutions used as controls for instruments that measure blood analytes. Disclosed herein is a novel flexible package for oxygen reference solutions.

The package is made from a laminated film comprising an inner layer with low or no oxygen reactivity, preferably polypropylene, aluminum foil as the middle layer, and an outer layer that protects the aluminum foil layer from physical damage, e.g., abrasion or corrosion. The seams are heat sealed, while an optional access device for allowing access to the solution after the storage period, is attached to the inside wall of the bag without breaching the laminated layers. The foil laminate packaging allows for mechanical simplicity.

Preferred tubing for conveying a multi-analyte reference solution with stable $pO_2$ from a container to a blood analyzer is also disclosed. Such tubing is flexible and relatively gas impervious, having a durometer (Shore D scale) in the range of 10 to 100, preferably from 70 to 94 and more preferably from 80 to 84. Preferred for such tubing are polyamide condensation polymers, more preferred are polyester/polyether block co-polymers or polyester elastomers, and especially preferred are Nylon™ [DuPont; Wilmington, Del. (USA)] and Hytrel™ 8238 [DuPont].

Another object of this invention is to provide multi-analyte reference solutions with stable $pO_2$ in zero headspace containers, wherein the solutions are stable at room temperature for at least six months, preferably for at least nine months, more preferably for at least about a year, still more preferably for more than a year, and even more preferably for from two to up to three years. The most unstable component of a multi-analyte reference solution in a zero headspace environment used for oxygen determinations, among other analyses, is usually the $pO_2$. Methods are provided to maintain the $pO_2$ of such a multi-analyte references solution within a predetermined range. Central to those methods is the principle of minimizing contact of the oxygen in the reference solution with materials that are oxygen reactive.

The lining of the preferred foil laminate packaging of this invention that contains the multi-analyte reference solutions with stable $pO_2$ of this invention is selected for its low reactivity to oxygen. The preferred polypropylene lining of the foil laminate package, preferably a foil laminate pouch, was chosen as it is essentially inert to oxygen.

Further, source materials, particularly organic source materials, for the other components of the multi-analyte reference solutions with stable $pO_2$ of this invention are also screened for low oxygen reactivity. It was found that some source materials contain impurities that are oxygen reactive enough to destabilize the $pO_2$ of such multi-analyte reference solutions.

It is further an object of this invention to prepare a panel of multi-analyte reference solutions with stable $pO_2$ that control from about 5 to about 20 analytes in as few containers as practicable, for example, a quality control reagent in five foil laminate containers (a 5 level QC reagent), wherein there is a different formulation in each zero headspace container. Key to combining so many critical analytes in as few containers as practicable are (1) using a low pH/low $pO_2$/low glucose/low tHb formulation as an all-inclusive level; and (2) separating the mid-$pO_2$ and high-$pO_2$ reference solutions from glucose and from the dyes needed to simulate tHb and/or CO-Ox fractions, A pH range considered low for the multi-analyte reference solutions of this invention is from about 6.4 to about 7.4. Exemplary of a low $pO_2$ range is from about 20 mmHg to about 75 mmHg. Exemplary of a mid-$pO_2$ to high poarange is from about 80 mmHg to about 600 mmHg. An exemplary low glucose concentration is from about 10 mg/dL to about 80 mg/dL. An exemplary low dye concentration corresponds to a tHb concentration of from about 5 g/dL to about 11 g/dL.

Methods of preparing such reagents are disclosed as well as the reagents prepared by those methods. Further disclosed are representative embodiments of such a quality control reagent constituting five formulations (a 5 level QC reagent).

Although exemplified herein are uses for the multi-analyte reference solutions laminate with stable $pO_2$ in zero headspace containers of this invention in the clinical field, they may also be used in the environmental and biotechnological fields, among other fields that require oxygen analysis. For example, the solutions of this invention would be useful in fermentation analyses.

BRIEF DESCRIPTION OF THE DRAWINGS

FIG. 1c is a first end view of the package of FIG. 1a.

FIG. 4b is a top view of the device of FIG. 4a. FIG. 4c is a side view of the device of FIG. 4a.

| ABBREVIATIONS AND BRAND NAMES | |
|---|---|
| AQC | automated quality control reagent |
| Brij 700 ™ | polyoxyethylene 100 stearyl ether with 0.01% BHA and 0.005% citric acid as preservatives, [surfactant from ICI Americas, Inc., Wilmington, DE, USA] |
| CDC | Chiron Diagnostics Corporation (formerly Ciba Corning Diagnostics Corporation) |
| COHb | carboxyhemoglobin |
| CO-Ox | CO-Oximeter or CO-Oximetry for instrument and method, respectively of measuring total hemoglobin and hemoglobin fractions, such as, $O_2Hb$, MetHb, COHb, SHb and HHb |
| Cosmocil CQ™ | polyhexamethylene biguanide hydrochloride, 20% [biocide from Zeneca Biocides, Wilmington, DE (USA)] |
| Dantogard ™ | 32% 1,3-bis(hydroxymethyl)-5,5-dimethylhydantoin and 7.5% hydroxymethyl-5,5- |

| -continued | |
|---|---|
| ABBREVIATIONS AND BRAND NAMES | |
| | dimethylhydantoin, in water [biocide from Lonza, Inc., Fair Lawn, NJ, (USA)] |
| EDTA | ethylene diamine tetraacetate |
| Hct | hematocrit |
| HDPE | high-density polyethylene |
| HEPES | 2-[4-(2-hydroxyethyl)-1-piperazinyl] ethanesulfonic acid [pKa of 7.31 at 37° C.] |
| HHb | reduced hemoglobin |
| HIDA | N-(2-hydroxyethyl)iminodiacetic acid |
| ISE | ion-selective-electrode |
| LLDPE | linear low-density polyethylence |
| M288 | Model 288 Blood Gas Analyzer [Chiron Diagnostics Corporation; Medfield, MA (USA)] |
| MetHb | methemoglobin |
| MIT | methylisothiazolone [a biocide from Boehringer-Mannheim GmBH, Indianapolis, Ind. (USA)] |
| MOPS | 3-(N-morpholino)propanesulfonic acid [pKa of 7.01 at 37° C.] |
| M. Yellow 7 | Mordant Yellow 7 |
| $O_2Hb$ | oxyhemoglobin |
| P.B. Violet | Patent Blue Violet |
| PE | polyethylene |
| $pCO_2$ | partial pressure of carbon dioxide |
| $pO_2$ | partial pressure of oxygen |
| PP | polypropylene |
| ProClin 300 ™ | 2.3% of 5-chloro-2-methyl-4-isothiazolin-3-one and 0.7% of 2-methyl-4-isothiazolin-3-one with 3% alkyl carboxylate in 94% of a modified glycol [biocide from Rhom & Haas Co., Spring House, PA (USA)] |
| PSI | pounds per square inch |
| PVC | polyvinylchloride |
| PVF | polyvinylfluoride |
| QC | quality control |
| Saran ™ | polyvinylidene chloride [Dow Chemical Company, Midland, MI (USA)] |
| SHb | sulfhemoglobin sulforhodamine B (dye; CAS #3520-42-1) |
| tHb | total hemoglobin |
| TTF | time to failure |

DESCRIPTION OF INVENTION

Foil Laminate Packaging

In one aspect, this invention concerns novel flexible packaging for oxygen reference solutions. Typical oxygen reference solutions used in whole blood analyzers comprise sodium, potassium, and calcium chloride salts, pH buffer, sodium bicarbonate, calcium chelating agent, surfactant, and biocide, which are equilibrated under partial vacuum with a carbon dioxide/oxygen gas mixture before filling. The typical oxygen partial pressures are from about 30 up to about 700 mmHg, but partial pressures as high as 2000 mmHg (i.e., greater than ambient) can be used, as well as partial pressures as low as zero (no oxygen present).

The packaging described herein stabilizes the oxygen reference solutions via the use of a multilayered film as the packaging material. In addition, the package incorporates an unusual access device for removing the solution. The access device is not exposed to the outside of the container. Instead it is sealed within the container and, as a result, does not provide an opportunity for there to be leakage around the seal during the pre-use storage as opposed to having the access device sealed within the package seam or through the wall of the container, where one would ordinarily expect it to be sealed.

The foil laminate packaging described herein is novel. First, the packaging material is selected because of the non-reactivity of its inner layer with oxygen. Second, the thickness of its layers are different from those of previous flexible packages. Third, the package described hereon has an optional, novel valve or access device, which reduces the amount of leakage and better maintains the integrity of the contents of the container. Fourth, all prior art in this area of technology was based on 4-sided bags with the security of one continuous seal around the entire perimeter of the package; whereas disclosed herein is a 3-sided, center-seal pouch having in places two, in other places four, layers of laminate to seal through, and six stress points per bag where laminate is folded at 360° and where one might therefore expect that a thin channel allowing gas exchange might result.

The foil laminate packaging of this invention is filled under vacuum without any headspace of gas above the oxygen reference liquid in order to make the contents insensitive to temperature and barometric pressure changes. A suitable fill volume would be between 10 and 1000 mL, and preferably about 20 to 250 mL.

Below under the heading Film, the multilayered foil laminate packaging is described in detail. The access device is similarly described in detail below under the heading The Access Device.

Multi-analyte Reference Solutions with Stable $pO_2$

In another aspect, this invention concerns methods of preparing multi-analyte reference solutions with stable $pO_2$ in zero headspace containers, preferably in the flexible foil laminate packaging described herein. The phrase "multi-analyte reference solution with stable $pO_2$" is herein defined to mean a reference solution used as a calibrator or as a control for $pO_2$ plus one or more other analytes, wherein the $pO_2$ of said reference solution is maintained within a predetermined range. Exemplary of such a range is at a specified value ±4 mmHg, alternatively at a specified value±2%, preferably±1%.

Examples of multi-analyte reference solutions with stable $pO_2$ include the following: (1) a blood gas reference solution with a stable $pO_2$ which calibrates or controls for $pO_2$, pH and $pCO_2$; (2) a blood gas and electrolyte reference solution which calibrates or controls for $pO_2$, pH, $pCO_2$ and electrolytes, such as, $Na^+$, $Cl^-$, $K^+$, $Ca^{++}$, $Li^+$ and $Mg^{++}$; (3) a blood gas/electrolyte and metabolite reference solution which calibrates or controls for $pO_2$, pH, $pCO_2$, electrolytes, and metabolites, such as, glucose, lactate, bilirubin, urea and creatinine; (4) a blood gas/electrolyte/metabolite and tHb reference solution; (5) a blood gas/electrolyte/metabolite/tHb and Co-Ox fraction reference solution; (6) reference solutions used for oxygen determination and to control or calibrate for one or more other analyte(s) selected from pH, $CO_2$, electrolytes, metabolites, tHb, CO-Ox fractions, and Hct.

Exemplary of $pO_2$ ranges calibrated or controlled by the multi-analyte reference solutions with stable $pO_2$ of this invention are those between 0 to 1000 mmHg, 20 to 700 mmHg and 30 to 500 mmHg. Exemplary $pCO_2$ ranges calibrated or controlled by the multi-analyte reference solutions of this invention that test for blood gas are those between 0 to 150 mmHg, 5 to 100 mmHg and 15 to 75 mmHg.

Described below under the heading Methods of Preparing Multi-Analyte Reference Solutions With Stable $pO_2$ are methods for maintaining the $pO_2$ of an multi-analyte reference solutions with stable $pO_2$ within a predetermined range for a desirable shelf life of from one to about three years.

Described below under the sub-heading Analyte Levels and Formulations of Representative QC and Calibrator Reagents, are exemplary and preferred five level QC reagents of this invention. Parameters of a key all-inclusive level (exemplified by level 3 below) are set forth under that sub-heading.

Methods of Preparing Multi-Analyte Reference Solutions With Stable $pO_2$

The most unstable component of a multi-analyte clinical reference solution in a zero headspace container used for oxygen determinations, among other determination(s), is usually $pO_2$. Methods are provided to maintain the $pO_2$ of multi-analyte reference solutions in a zero headspace container within a predetermined range, that is, e.g., at a specified value ±4 mmHg, alternatively ±2%, preferably at±1%.

Central to the methods of maintaining the stability of $pO_2$ in multi-analyte reference solutions in zero headspace containers is minimizing the contact of the oxygen in such a reference solution with materials that are oxygen reactive. As detailed infra, the lining of the foil laminate packaging for multi-analyte reference solutions with stable $pO_2$ of this invention is selected for its low reactivity to oxygen. PP is the preferred lining material for the flexible zero headspace packaging of this invention.

Further the methods of this invention for preparing multi-analyte reference solutions with stable $pO_2$ comprise preparing such reference solution formulations with components that have been screened for low or no oxygen reactivity. A representative raw material screening process is provided below. Particularly important is the screening of organic materials for low or no oxygen reactivity. It was found, as shown below, that some source materials may contain impurities that are oxygen reactive enough to destabilize the $pO_2$ of such a multi-analyte reference solution in a zero headspace container.

Further are provided methods of preparing multi-analyte reference solutions with stable $pO_2$ in the least number of zero headspace containers for detecting as many critical care analytes as practicable. Set forth below are examples of such formulations. Again low oxygen reactivity is critical to preparing stable formulations. It is important to formulate an all-inclusive level, wherein the $pO_2$ is low, for example, at 30 mmHg, 40 mmHg or at 50 mmHg, at a low pH, for example, at pH 7.13 or 7.15, and at a low glucose concentration, for example, at 46 or 50 mg/dL, and at a low dye concentration.

Further in regard to other levels of such a reagent, it is important to separate the formulations used to test for mid-$pO_2$ and high-$pO_2$ from glucose and from the dyes needed to simulate tHb and CO-Ox fractions. Exemplary formulations are provided below.

Analyte Levels and Formulation of Representative QC and Calibrator Reagents

It is desirable to prepare a minimum number of formulations for the multi-analyte reference solution panels of this invention, [i.e., preferred quality control (QC) reagents] so that, test time on analyzers is maximized and costs are minimized. However, the lack of headapace in the packaging of this invention renders that goal of minimizing the number of formulations to test a maximum number of analytes difficult in that unlike the conventional glass ampule packaging which has on a volume-to-volume basis, roughly 32 times more oxygen in the headspace than in solution, the packaging of the instant invention has no oxygen reserve. Without an oxygen reserve, organic materials in the solutions, such as, glucose and the dyes used to simulate hemoglobin, or impurities in such source materials, react with the oxygen present in the solutions, thereby reducing the $pO_2$ of the solutions.

Key to combining so many critical analytes in as few containers as practicable are (1) using a low pH/low $pO_2$/low glucose/low tHb formulation as an all-inclusive level (exemplified by level 3 herein); and (2) separating the mid-$pO_2$ and high-$pO_2$ reference solutions from glucose and from dyes. Exemplary formulations for a five level quality control reagent are provided below. Such a five level QC combines from about 5 to about 20 analytes, preferably from about 12 to about 20 analytes including pH, $pO_2$, $pCO_2$, electrolytes, metabolites, hematocrit, tHb, and CO-Ox fractions. The all-inclusive level of such a QC reagent controls for the following analyte levels:

(1) a low pH, from about 6.4 to about 7.4, more preferably from about 6.8 to about 7.3, still more preferably from about 7.1 to about 7.2;

(2) a $pO_2$ of from about 20 mmHg to about 75 mmHg, more preferably from about 25 mmHg to about 70 mmHg, and still more preferably from about 30 mmHg to about 60 mmHg; and (3) a low glucose concentration of from about 10 mg/dL to about 80 mg/dL, more preferably from about 30 mg/dL to about 60 mg/dL; and (4) contains a low dye concentration corresponding to a hemoglobin concentration of about 5 g/dL to about 11 g/dL, preferably from about 6 g/dL to about 10 g/dL, more preferably from about 7 g/dL to about 9 g/dL.

Table 1 below shows exemplary analyte levels for a representative 5 level automatic quality control reagent ("5 Level AQC") of this invention.

TABLE 1

Exemplary Analyte Levels for 5-Level AQC

| | Analyte | | | | |
|---|---|---|---|---|---|
| | 1 | 2 | 3 | 4 | 5 |
| pH | 7.55 | 7.35 | 7.15 | | |
| $pCO_2$, mmHg | 20 | 40 | 70 | | |
| $pO_2$, mmHg | 150 | 100 | 50 | | |
| $Na^+$, mmol/L | 155 | 135 | 115 | | |
| $K^+$, mmol/L | 7.0 | 5.0 | 3.0 | | |
| $Ca^{++}$, mmol/L | 0.8 | 1.2 | 1.6 | | |
| $Mg^{++}$, mmol/L | 0.4 | 0.6 | 1.0 | | |
| $Cl^-$, mmol/L | 120 | 100 | 80 | | |
| Lactate, mmol/L | | | 3 | 1 | 12 |
| Glucose, mg/dL | | | 50 | 100 | 200 |
| Urea, mg/dL | | | | 12 | 70 |
| Creatinine, mg/dL | | | | 1.0 | 7.0 |
| Bilirubin, mg/dL | | | 3 | 15 | 2S |
| tHb, g/dL | | | 8 | 14 | 18 |
| $O_2Hb$, % | | | 60 | 92 | 80 |
| COHb, % | | | 18 | 3 | 3 |
| MetHb, % | | | 6 | 2 | 14 |
| HHb, % | | | 16 | 3 | 3 |
| Hct, % | | | | 45 | 25 |

It is further preferred that analyte levels of the reference solutions include not only tHb as an analyte, but also the other CO-Ox fractions—$O_2Hb$, COHb, MetHb SHb and HHb as shown in Table 1. Therefore, 16 analytes are controlled by the representative all-inclusive level (Level 3) as follows:

| Blood Gas | pH, $pCO_2$, $pO_2$ |
|---|---|
| Electrolytes | $Na^+$, $K^+$, $Ca^{++}$, $Mg^{++}$, $Cl^-$ |
| Metabolites | Glucose, Lactate, Bilirubin |
| CO-Ox | tHb, $O_2Hb$, COHb, MetHb, HHb. |

Table 2 sets forth representative formulations that could be used to prepare a 5-level AQC. It is preferred that Hct, creatinine and urea only be monitored at two levels, whereas the other analytes are monitored at three levels in five formulations.

TABLE 2

Representative Formulations for 5-Level AQC

| | 1 | 2 | 3 | 4 | 5 |
|---|---|---|---|---|---|
| MOPS: mmol/L | 30 | 30 | 27 | 10 | 30 |
| NaOH: mmol/L | 29 | 28 | 27 | 12 | 26 |
| $NaHCO_3$: mmol/L | 21 | 21 | 21 | 6 | 6 |
| NaCl: mmol/L | 115 | 95 | 75 | 14 | 32 |
| KCl: mmol/L | 7.9 | 5.7 | 3.4 | 4 | 4 |
| Citric Acid: mmol/L | 1.5 | 2.0 | 2.5 | 2.0 | 2.0 |
| $CaCl_2$: mmol/L | 1.8 | 2.4 | 3.4 | 2.4 | 2.4 |
| $Mg^{++}$ (Acetate-)$_2$: mmol/L | 0.9 | 1.2 | 2.0 | 1.2 | 1.2 |
| $Li^+Lactate^-$: mmol/L | | | 3.0 | 1.0 | 12.0 |
| Glucose: g/L | | | 0.50 | 1.00 | 2.00 |
| SRB (red dye): g/L | | | 0.490 | 0.924 | 1.104 |
| M. Yellow 7: g/L | | | 0.249 | 1.770 | 0.786 |
| FD&C Blue #1: g/L | | | .0027 | | .0259 |
| P.B. Violet: g/L | | | | 0.103 | |
| Creatinine: g/L | | | | .0100 | .0700 |
| Urea: g/L | | | | 0.257 | 1.50 |
| Brij 700 ™: g/L | .05 | .05 | .05 | .05 | .05 |
| MIT: g/L | .40 | .40 | .40 | 0.40 | 0.40 |
| Tonometry gas % $CO_2$/% $O_2$/Bal. $N_2$ | 6/48 | 10/25 | 17/5 | 6/48 | 6/48 |

Exemplary Preferred All-inclusive Level (Level 3) Formulation

A preferred all-inclusive level (designated Level 3 herein) formulation of a 5-Level AQC would control from about 5 to about 20 analytes, preferably from about 12 to about 18 analytes, more preferably from about 14 to about 16 analytes. The following is an exemplary preferred formulation which includes 14 components:

| 1. MOPS | 30 mmol/L | 8. Glucose | 2.8 mmol/L |
|---|---|---|---|
| 2. NaOH | 25 mmol/L | 9. Citric Acid | 2.0 mmol/L |
| 3. $NaHCO_3$ | 20 mmol/L | 10. SRB | 0.49 g/L |
| 4. NaCl | 75 mmol/L | 11. Mordant Yellow 7 | 0.25 g/L |
| 5. KCl | 3.4 mmol/L | 12. FD&C Blue 1 | 0.003 g/L |
| 6. $CaCl_2$ | 3.0 mmol/L | 13. Brij 700 | 0.05 g/L |
| 7. $Li^+$Lactate | 3.0 mmol/L | 14. ProClin 300 | 0.5 g/L |

Accelerated stability studies are disclosed below for that preferred all-inclusive (Level 3) formulation.

The following analyte levels were obtained with that preferred all-inclusive (Level 3) formulation:

| pH | 7.13 | $Na^+$ | 120 mmol/L | tHb | 8.2 g/dl |
|---|---|---|---|---|---|
| $pCO_2$ | 67 mm | $K^+$ | 3.3 mmol/L | $O_2Hb$ | 14% |
| $pO_2$ | 34 mm | $Ca^{++}$ | 1.48 mmol/L | COHb | 70% |

-continued

| Glucose | 46 mg/dL | Cl⁻ | 87 mmol/L | MetHb | 1% |
|---|---|---|---|---|---|
| Lactate | 3 mmol/L | | | Hbb | 14%. |

Bags from throughout the lot were randomly selected and stressed at elevated temperatures for appropriate time intervals in order to perform an accelerated stability study and generate an Arrhenius plot to predict shelf life at room temperature. The methods used were similar to those described infra. Results for $pO_2$, the least stable analyte, are shown in Table 3.

TABLE 3

Accelerated Stability of an Exemplary Level 3 Formulation

| Temperature, °C. | Time, wks | $\Delta pO_2$ v. control, mmHg |
|---|---|---|
| 55 | 1 | −4.3 |
|  | 2 | −6.4 |
| 50 | 2 | −1.8 |
|  | 6 | −4.0 |
| 45 | 6 | −3.3 |
|  | 10 | −4.4 |
| Allowable Change |  | ±4 |

The table below shows the Arrhenius calculations used to derive the estimated shelf life.

TABLE 4

Arrhenius Calculations for a Preferred Level 3 Formulation

| Temperature, °C. | 1/K | Time-to-Failure, wks | Log(ttf) |
|---|---|---|---|
| 55 | .0030488 | 1.1 | 0.055 |
| 50 | .0030960 | 5.8 | 0.77 |
| 45 | .0031447 | 8.5 | 0.93 |
| 25 | .0033557 | 875 | 2.94 |

The projected room temperature shelf life of 875 weeks, or 17 years, for the representative Level 3 formulation was estimated using 0.94 as the correlation coefficient. A more conservative estimate can be made using a rule-of-thumb which relies on the fact that the minimum change in reaction rate per 10° C. increase in reaction temperature is an increase of two times. Based on failure in 2 months at 45° C., the inventors would estimate that failure will not occur at 25° C. until at least 8 months. However, the inventors consider it highly unlikely that the reaction-rate increase per 10° C. increase would be any less than three times. Therefore, the inventors consider that a realistic but still conservative estimate of the shelf life of the representative Level 3 formulation would be at least 18 months.

Formulation Preparation

To prepare the formulations of this invention, all solutions require tonometry with the appropriate gases to achieve the gas levels listed above. Although gas values are not always listed above for levels 4 and 5, tonometry is still desirable in order to achieve gas levels which minimize hysteresis and drift effects on the gas sensors.

The tonometry can be performed at temperatures such as 25° C. or 37° C. or even 50° C., and of course the choice of temperature will affect the composition of the tonometry gas. More importantly, tonometry should be performed at sub-atmospheric pressures, preferably in the 300–500 mmHg range, so that outgassing will not occur if the solutions are used at high altitudes where the barometric pressure is below normal, or in warm environments. Obviously, the higher the tonometry temperature, the higher the pressure allowed in the tonometer. An example of a suitable condition is 37° C. at 450 mmHg, where the gas composition for a level 2 QC would be 10% $CO_2$, 25% $O_2$ and 65% $N_2$.

Exemplary preferred dyes for the formulations of this invention are listed in Table 2, supra. Those dyes are disclosed in Li, J., EP 0 743 523 A2 (published Nov. 20, 1996), Buffers HEPES and MOPS are preferred buffers for the formulations of this invention. MOPS is a particularly preferred buffer. Other suitable buffer systems, including the sodium salt derivatives, are described by Good et al., *Biochemistry*, 5: 467–477 (1966) and Ferguson et al., *Analytical Biochemistry*, 104: 300–310 (1980).

Shelf Life and Use Life

One object of this invention is to increase the shelf life and use life of the QC and calibrator formulations of this invention. An acceptable shelf life (i.e., closed package) would be about one year. A preferred shelf life would be from about one year to two years, and still more preferred from about one to three years.

An acceptable use life (i.e., open package) would be about two weeks, preferably from about two weeks to about a month, and more preferably from about two weeks to about two months. The use life is extended by appropriate selection of tubing material to conduct reference solutions from the access device to the blood analyzer as described infra.

The inventors discovered a critical element in how the formulations impact shelf life by de-stabilizing $pO_2$. One study compared a very simple formulation, containing only sodium bicarbonate to neutralize the $CO_2$ in the tonometry gas, and Brij 700 surfactant, to create appropriate surface tension, such that the solution behaves normally in the tonometer and filler, to a complete 10-ingredient formulation. The data are summarized in Tables 5 and 6.

TABLE 5

Accelerated Stability of 2- vs 10-Ingredient Formulation: $\Delta pO_2$, mmHg from control

| Temp | Time, wks | Only Brij + Bicarb | +8 Other Chemicals |
|---|---|---|---|
| 60° C. | 1 | −5.3 | −14.0 |
| 55° C. | 1 | −2.4 | −7.7 |
|  | 2 | −5.6 | −15.4 |
| 50° C. | 1 | −2.6 | −3.3 |
|  | 2 | −2.7 | −12.4 |
| 45° C. | 2 | +0.2 | −4.7 |
| Allowable Change |  | ±4.4 | ±4.4 |

TABLE 6

Arrhenius Calculation Based on $pO_2$ Data for Formulations in Table XVI

| Temp | 1/K | Bicarb + Brij | | +8 Chemicals | |
|---|---|---|---|---|---|
| | | Time-to-failure | Log(ttf) | Time-to failure | Log(ttf) |
| 60° C. | .0030030 | 5.8 days | 0.763 | 2.2 days | 0.342 |
| 55° C. | .0030488 | 11.3 days | 1.054 | 4.0 days | 0.602 |
| 50° C. | .0030960 | 22.8 days | 1.356 | 7.1 days | 0.854 |
| 45° C. | .0031447 | | | 13.1 days | 1.117 |
| 25° C. | .0033557 | 1042 days | 3.018 | 185 days | 2.268 |

The correlation for the Arrhenius prediction for the 2-component formulation was 0.99999, and for the 10-component formulation, 0.9999 (r). It can be seen that addition of eight additional chemicals, the inorganic compounds NaCl, KCl, $CaCl_2$, NaOH, and the organic compounds citric acid, glucose, MOPS (pH buffer),and ProClin 300 (biocide), caused the $pO_2$ to be less stable by 5–6 times as compared to the simple, 2-component formulation. The shelf life estimate for 25° C. decreased from 34 months for the 2-component formulation to 6 months for the 10-component formulation. Thus, some or all of the eight added chemicals reacted with oxygen in the aqueous solution in the flexible bag, causing premature loss of shelf life.

Therefore, studies by the inventors have shown that it is difficult to achieve stable $pO_2$ in a zero-headspace package with formulations having many ingredients, each potentially capable of reacting with oxygen, and realizing that interactions among ingredients could also be de-stabilizing. Specifically, test results suggest that glucose and the dyes used to simulate hemoglobin can react with oxygen. The oxygen reactivity of those chemicals is one reason the inventors prefer to separate those chemicals in QC levels 4 and 5 from QC levels 1 and 2. However, the inventors realize that the QC all-inclusive level (level 3) includes those 3 analytes along with the other nine analytes, but determined that that all-inclusive level 3 formulation should work because:

1. at pH 7.15, glucose is more stable than at the two higher pH levels;
2. the levels of glucose and Hb-simulating dye are all low; and
3. the $pO_2$ is low. In fact, the true $pO_2$ at the low level is roughly half of the measured $pO_2$.

Thus, the inventors discovered that the unique properties of level 3 allow the packaging of a QC in 5 containers rather than 6, provides the advantage to the customer of more patient samples to be assayed in a given time period.

Direct Comparison of $pO_2$ Stability in Zero Headspace Packaging v. Ampules A study was performed to compare a conventional multi-analyte QC formulation, similar to the formulation in Table A of U.S. Pat. No. 5,637,505, in glass ampules to that same formulation in a zero headspace foil laminate package of this invention. To achieve roughly the same $pCO_2$ and $pO_2$ values in the foil laminate packaging process, as occur in the ampuling process, the foil laminate pouches were filled with QC solutions that were tonometered under partial vacuum with the appropriate gases, and then the solutions were pumped into zero-headspace foil laminate pouches, and pasteurized as set forth below. A limited accelerated stability study was then performed in accordance with the method described above. The two studies allowed us to make the following comparison:

TABLE 7

Comparison of Packages with and without Headspace
Values below are $\Delta pO_2$, mmHg (except for factors)

| Condition | | Level 2 | | | Level 3 | | |
|---|---|---|---|---|---|---|---|
| Temp, °C. | Time, wks | Ampules | Bags | Factor | Ampules | Bags | Factor |
| 45 | 2 | −1.2 | −36 | 30X | −0.9 | −12 | 14X |
| 50 | 2 | −1.0 | −42 | 42X | | | |
| 55 | 1 | −2.6 | −53 | 20X | −1.3 | −21 | 16X |
| 60 | 2 | | | | −1.9 | −57 | 30X |

It can be seen that there is a considerable range among the six factors, from a low of 14× to a high three times as great, 42×. What can be concluded from the data is that maintaining $pO_2$ stability in a relatively inert, zero headspace package is at least an order of magnitude more difficult than maintaining the same degree of $pO_2$ stability in a package with a headspace at least half as large as the solution volume.

Raw Material Screening Test

A representative screening test for the components of formulations of this invention is demonstrated by the study of this section. Ten solutions with the same defined level of $pO_2$, were prepared simultaneously by equilibrating deionized water in glass containers at 50° C. in a water bath. The temperature of the water bath must be at least as high as the temperature intended to be used for the accelerated test which is to follow, so as to avoid out-gassing of oxygen during the stress cycle at elevated temperature.

In order to magnify the oxygen consumption of individual ingredients, especially in cases where there may be several minor contributors as opposed to one or two major contributors, it is desirable to increase the concentrations above their normal use levels. In this study, the inventors increased concentrations by. five times.

The inventors isolated the eight chemicals added to the two component formulations in the study described above under the heading Shelf Life and Use Life. Those eight chemicals are the inorganic compounds NaCl, KCl, $CaCl_2$, NaOH, and the organic compounds, citric acid, glucose, MOPS (pH buffer) and ProClin 300 (biocide). However, in order to test in the neutral pH range (6–8) some chemicals had to be tested together, namely, MOPS with NaOH, and citric acid with sodium bicarbonate. For efficiency, the three chloride salts were tested together, based on our prediction that the inorganic chemicals were unlikely to be significant contributors to slow oxidation reactions. In addition to the eight chemicals already mentioned, we also tested an alternative pH buffer, HEPES, and two dyes, SRBand Mordant Yellow 7.

Chemicals were added to the pre-warmed deionized water in glass bottles, and mixed by inversion. When all chemicals in all bottles were dissolved, solutions were poured into bags which had been sealed on 3 sides, followed immediately by sealing the fourth side below the liquid level. After a 44 hr/65° C. pasteurization step, half of the bags were left at room temperature while the other half were stressed for twelve days at 50° C., followed by cooling to room temperature. Controls and stressed bags were tested for $pO_2$ in one run on two model 288s. The following results were obtained:

TABLE 8

Screening Test of Chemical Ingredients for Oxygen Reactivity

| Substance | Mean $\Delta pO_2$ | Range |
| --- | --- | --- |
| Water blank | −4 mmHg | 4 mmHg |
| MOPS, Sigma | −5 | 4 |
| MOPS, Research Organics | −4 | 4 |
| Glucose, Sigma | −14 | 3 |
| Glucose, Fluka | −11 | 3 |
| ProClin 300, lot LA60507 | −7 | 2 |
| ProClin 300, lot LA64543 | −9 | 4 |
| Citric Acid, Bicarbonate, Brij | −9 | 10 |
| NaCl, KCl, $CaCl_2$ | −5 | 4 |
| HEPES (pH buffer) | −6 | 3 |
| Sulforhodamine B (red dye) | −6 | 8 |
| Mordant Yellow 7 (dye) | −13 | 5 |

Those results show that:

1. glucose and Mordant Yellow 7 are the most significant oxygen reactives;
2. ProClin 300 is moderately reactive;
3. MOPS, HEPES, and the three chloride salts are relatively non-reactive; and
4. results for SRB and the citric/bicarb/Brij mixture were non-conclusive due to excessive bag-to-bag variability. However, further substantially similar screening showed that SRB was moderately reactive, and that citric acid, sodium bicarbonate and Brij were relatively non-reactive.

In regard to Mordant Yellow 7, shown above to be significantly oxygen reactive, it can be concluded that it would be preferred that another yellow dye or Mordant Yellow 7 that is less oxygen reactive, e.g., from another source, be used in the formulations of this invention. When tHb is the only CO-Oximetry analyte to be tested, a red dye is sufficient.

SRB is a red dye, and the particular SRB screened was found to be moderately reactive. It may be preferred to screen SRBs from other sources or other red dyes for an SRB or other red dye having lower oxygen reactivity. However, the accelerated stability results in Table 4 show that the level 3 formulation containing the above-screened SRB and Mordant Yellow 7 dyes has significantly more than a year's shelf life. Shelf life of such a formulation may be further prolonged by screening and incorporating therein dyes having lower oxygen reactivity.

Effect of Glucose on $pO_2$ Instability

The strong destablizing effect of glucose on $pO_2$ stability was noted in the study described below. This study compared two sources of glucose, used at 1.8 g/L—one from Fluka Chemical Corp. [Ronkonkoma, N.Y. (USA)] and one from Sigma Chemical Co. [St. Louis, Mo. (USA)]—in a 150 mmHg $pO_2$ calibrator at pH 6.8 to the same calibrator without any glucose added. A limited accelerated stability test was conducted on those solutions, with the following outcome.

TABLE 9

Effect on $pO_2$ of Storing 150 mmHg Calibrator at High Temperatures for 2 wks

Mean difference from Non-heated solutions, mmHg

| TEMP | No Glucose added | Fluka Glucose added | Sigma Glucose added |
| --- | --- | --- | --- |
| 45° C. | −2.2 | −5.7 | −6.3 |
| 50° C. | −4.7 | −8.8 | −9.9 |

It can be seen that:

1. at both temperatures, both sources of glucose at least double the $pO_2$ decrease; and
2. the differences between the two glucose sources are relatively minor.

Thus, those results fit very well with the results reported in the section on screening raw materials above. Moreover, because the source appears to play a relatively minor role, this suggests that the oxygen reactivity is inherent in glucose, which was not obvious before we undertook this study.

There are at least three well-known degradation mechanisms for glucose:

1. reaction with oxygen, forming gluconic acid, if glucose oxidase is present;
2. reaction with ATP, forming glucose-6-phosphate, if hexokinase is present; and
3. alkaline rearrangement, forming first fructose, later mannose.

The first two are widely used in clinical chemistry assays to measure the level of glucose in blood. The third, occurring at even mildly basic pH, is the most common route for glucose instability in quality controls used in conjunction with glucose assays.

None of those three common reactions explain the presumed reaction between glucose and oxygen in the formulations of this invention because only one lists oxygen as a reactant, and in that case, the necessary enzyme is not present in our formulations. Moreover, stoichiometry between moles of glucose decrease and moles of oxygen decrease were not noted, and no 1:1 relationship was found.

TABLE 10

Stoichiometry of Oxygen v. Glucose Decomposition

| 200 | Cal | Glucose | | Oxygen | |
| --- | --- | --- | --- | --- | --- |
|  |  | mg/dL/wk | mmol/L/wk | mmHg/wk | mmol/L/wk |
| Lot 1645 | 50° C. | −0.78 | −.043 | −2.7 | −.004 |
|  | 45° C. | −0.41 | −.023 | −2.0 | −.003 |
| Lot 1655 | 50° C. | −0.71 | −.039 | −3.3 | −.005 |
|  | 45° C. | −0.35 | −.019 | −1.9 | −.003 |

It can be seen that the glucose loss is considerably greater than the oxygen loss. The additional glucose loss must be due to non-oxygen consuming reactions.

Film

The film which is used for the container is multilayered and uses a material having low or no oxygen reactivity, preferably polypropylene (PP), for the inner layer, aluminum foil for the middle layer, and an outer layer that is protective of the aluminum layer, preferably polyester. The outer layer merely provides protection for the aluminum layer, preventing abrasion and corrosion. Thus, for example, a nylon layer, or even a simple lacquer coating are suitable alternatives. [Nylon is a family of high-strength, resilient synthetic materials, the long-chain molecule of which contains the recurring amide group CONH. The term "nylon" was coined by its inventors at E.I. duPont de Nemours & Co., Inc.] However, the outer layer should have a melting point greater than PP's melting point which is about 170° C.

An important parameter of the aluminum layer is that it be thick enough so that there are no pinholes, thus preventing physical leakage of oxygen, yet thin enough so that it can be readily formed into pouches on automated machines and will, after being filled, release its contents without undo force by readily collapsing as the contents are removed.

The inner PP layer is important for several reasons. First, it must melt and form the seal which closes the package. Second, it must be unreactive with the oxygen. It is this second factor which distinguishes this packaging material from those previously used for this purpose.

To the inventors' knowledge, this laminate has never been used commercially for packaging products which contain high-precision solutions with dissolved gases for scientific, medical, analytical purposes. The PP lined laminate is not known to be used by others as an oxygen barrier for chemical products. A former manufacturer of oxygen calibrators (Mallinckrodt Sensor Systems, Inc., Ann Arbor, Mich.) has used laminated film to package a calibrator, but they used polyethylene as the inner, sealing layer. The PP lined laminate has been used in the past mainly for food products, and has been chosen for the high melting point of the polypropylene sealing layer, which makes this material suitable for sterilization in a steam autoclave or similar equipment.

Films from various suppliers were evaluated for efficacy in maintaining the dissolved gas concentrations of solutions stored within. Films were obtained from Kapak Corp., Minneapolis, Minn. (part no. 50703), American National Can Co., Mount Vernon, Ohio (part nos. M-8309, M-8359, M-8360), James River Corp., Cincinnati, Ohio (part nos. JR 4123, JR 4400), Technipaq, Inc., Crystal Lake, Ill. ("Dull Foil Laminate"), Lawson Mardon Flexible, Inc., Shelbyville, Ky. (spec nos. 13362 and 15392), Smurfit Flexible Packaging, Schaumburg, Ill. (LC Flex 70459, 70464), and Rollprint Packaging Products, Inc., Addison, Ill. (RPP #26-1045). 4-sided bags were either purchased with 3 sides pre-sealed or were formed using an impulse heat sealer from Toss Machine Components, Inc., Bethlehem, Pa., Model 01617. The 3-side sealed bags were filled with various reference solutions and immediately sealed through the liquid, allowing no headspace inside the package. In some instances, for enhanced stability of the oxygen partial pressure in the reference solution stored within the bags, filled, sealed bags were heat-treated at elevated temperatures between approximately 50° C. and 121° C. for times ranging from 15 minutes to 7 days, depending on the temperature.

Figure 1A:
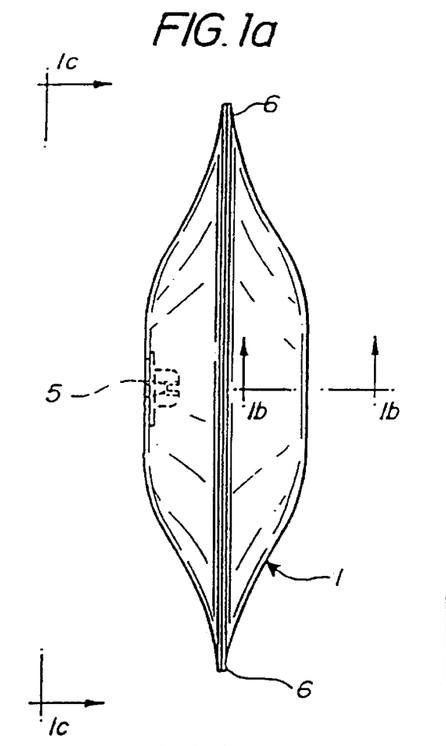
FIG. 1a is a side view of a four-sided multilayer package of this invention.
Figure 1B:
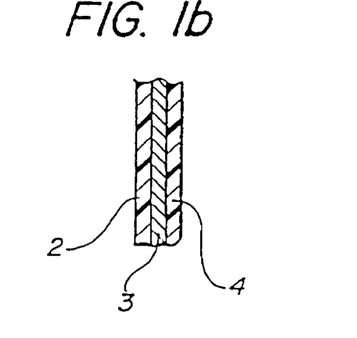
FIG. 1b is a cross-sectional view showing three layers of the packaging.

FIG. 1a shows a side view of a sealed bag 1, and one possible location of the access device 5 in the interior of the bag is shown. The sealed portion of the bag is also shown 6. FIG. 1b shows the 3 layers of a preferred film, the inner polypropylene layer 2, the middle aluminum layer 3, and the outer polyester layer 4.

Some filled bags were left at room temperature; others were stored at elevated temperatures for various times. To simplify reporting of this and subsequent trials, we used storage at 55° C. for 1 week as a basis for comparison. After removing test bags from the incubator, they were cooled to room temperature and tested on two critical care analyzers [generally selected from the 200 Series Critical Care Diagnostic Systems manufactured by Chiron Diagnostics Corporation; Medfield, Mass. (USA); a 278 was often used with a 288] with control bags in the same run. In particular, the $pO_2$ results were examined in a series of six studies. Due to differences in conditions such as reagent composition and package surface-to-volume ratios, the $pO_2$ differences are not directly comparable. Therefore, all results were converted to relative scores where the most stable laminate was assigned a score of 1.00, and all other laminates were assigned scores on the basis of $\Delta pO_2$ ratios. Using this convention, the following results were obtained:

TABLE 11

| Material | N | Mean Score | Range of Scores |
| --- | --- | --- | --- |
| Polyethylene | 4 | 0.14 | 0.10–0.16 |
| Polypropylene | 6 | 0.41 | 0.18–1.00 |
| Polyester | 2 | 0.28 | 0.26–0.30 |

The preferred and most preferred laminates have an inner PP liner of the thickness shown below, a middle layer of aluminum as shown below, and an outer polyester layer. (The thickness and material selection of the outer layer is least critical and can vary somewhat.) Acceptable film thicknesses are also shown. Approximate thicknesses of layers in mils (1/1000 inch):

TABLE 12

| | Polypropylene | Aluminum | Polyester |
| --- | --- | --- | --- |
| Most preferred | 4 mil | 0.5 mil | 0.5 mil |
| Preferred | 2–5 mil | 0.5–0.7 mil | 0.5 mil |
| Acceptable | 1.5–5 mil | 0.3–1.0 mil | 0.1–2 mil |

Other acceptable layers include polyester at 0.5–2 mil for the inner layer; for the outer layer either nylon with thickness of 0.2–2 mil or lacquer coating. Polyethylene has not been found to be acceptable as an inner layer.

There are detrimental properties that result if any of the film layers are too thick. Namely, the laminate becomes too rigid, making it difficult to form and fill during manufacture, and difficult to pump out the liquid contents from the pouch/bag during use. Furthermore, if the aluminum layer is too thin, there is a higher probability of having pin-holes, which may lead to gas leakage. If the sealing layer is too thin, it may be entirely displaced at the moment of heat-sealing at the seal under high pressure required for strong seals, thereby exposing bare aluminum which would react with oxygen.

Stability testing has shown that the PP lined film is preferred over the polyethylene film. The Arrhenius method of predictingproduct shelflife is well-established in the in-vitro diagnostics and pharmaceutical industries (Conners et al, "Chemical Stability of Pharmaceuticals: A Handbook for Pharmacists", NY: Wiley, 1986; Porterfield & Capone, MD&DI 45–50, April 1984; Anderson & Scott, *Clin Chem*, 37: 3, 398–402, 1991; Kirkwood, *Biometrics*, 33, 736–742, December 1977). Products are stored at elevated temperatures for various times, following which they are re-equilibrated at ambient temperature and tested against non-stressed controls for critical properties such as activity of a component or measured analyte. The rate of change or more conveniently, the time-to-failure, of a given analyte is determined for each temperature, often by plotting log(C/Co) vs time, which is a linear function for the most common, first-order reactions. Owing to the linear relationship between log(time-to-failure) and the inverse of the absolute temperature (1/K), a plot can be constructed from the elevated-temperature data, and the resulting line can be extended to the maximum recommended storage temperature to predict the time-to-failure at that temperature. In this manner, actual shelflife can be predicted in advance.

In an early predicted shelflife study using polyethylene-lined bags, finished packages filled with an oxygen reference solution were stored at 35, 45, and 55° C. for times ranging from 4 days to 8 weeks, depending on the storage temperature, using longer times with lower storage temperatures. Each test condition included 4 bags tested on two blood gas analyzers [200-series manufactured by Chiron Diagnostics Corp. (CDC), supra]. Time-to-failure (TTF) was defined as a 2% change in $pO_2$.

TABLE 13

Polyethylene (PE)

| Temperature | 1/K | Time-to-Failure | Log(ttf) |
| --- | --- | --- | --- |
| 55° C. | .0030488 | 0.6 weeks | −0.222 |
| 45 | .0031447 | 1.1 | 0.036 |
| 35 | .0032468 | 4.4 | 0.647 |

Regression analysis on the above data, based on plotting log(ttf) as a function of 1/K, results in a predicted 25° C. shelflife of 3 months for an oxygen reference solution stored in the polyethylene-lined bag. The correlation coefficient, r, is 0.98.

In the polypropylene study, finished packages containing an oxygen reference solution were stored at 35, 40, 45, and 50° C. for times ranging from 1 to 9 weeks, depending on the storage temperature, using longer times with lower temperatures. Each test condition included 3 bags tested in singlicate on two blood gas analyzers (200-series from CDC, supra). The first-order model was used to determine time-to-failure (TTFs), where failure was defined as a 2% change in $pO_2$.

TABLE 14

Polypropylene (PP)

| Temperature | 1/K | Time-to-Failure | Log(ttf) |
| --- | --- | --- | --- |
| 50° C. | .0030960 | 1.3 weeks | 0.106 |
| 45 | .0031447 | 3.3 | 0.521 |
| 40 | .0031949 | 5.7 | 0.755 |
| 35 | .0032468 | 12.3 | 1.091 |

Figure 5:
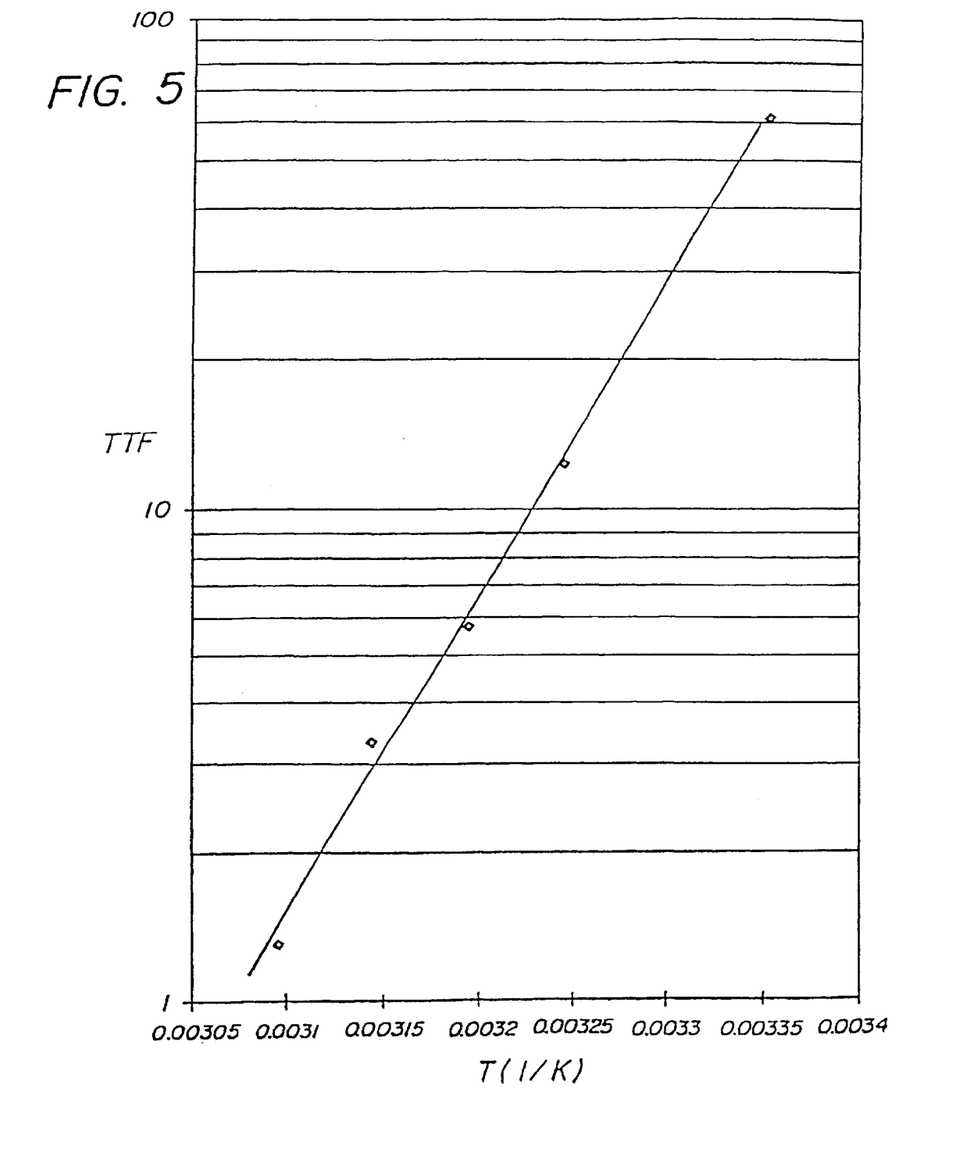
FIG. 5 is an Arrhenius diagram showing the predicted shelf life of a typical formulation contained in the novel packaging of this invention.

Using the four TTFS, an Arrhenius plot was constructed (see FIG. 5), where time to failure (in weeks) (TTF) is shown as a function of inverse temperature, 1/K (shown as T in FIG. 5). (1/K is the inverse of Kelvin temperature.) The linear extrapolation to 25° C. is 61 weeks or 14 months, for an average $pO_2$ change of −0.066mmHg/wk. The reliability of the prediction is affirmed by the highly linear relationship among the 4 points, with a correlation coefficient, r, of 0.99. A score of 1.00 would indicate that all points fall on a straight line; a score of 0.00, that no relationship exists between log ttf and 1/K. (Note that the equation for the Arrhenius plot exemplified was found to be log y=−19.48+6339x.)

The resulting predicted shelflife of the oxygen reference solution in polypropylene-lined bags represents a four-to-fivefold improvement over the shelflife predicted for oxygen reference solution stored in the polyethylene-lined bags. It also represents a nearly tenfold improvement over a recent stateof the art product, known as "Cal B" which was sold by Mallinckrodt Sensor Systems, Inc. [Ann Arbor, Mich. (USA)]. The software in the GEM® Premier Analyzer that accompanies that system automatically subtracts 0.58 mmHg $pO_2$ from the initial assigned $pO_2$ for every week which has elapsed since manufacturing in order for the Cal B calibrator to be useable for its expected commercial usage period. If not for this calculation, using our 2% criterion, the useful shelflife would be only 7 weeks, clearly too short a time for commercial use of the product. Moreover, note that the actual Cal B shelflife, 6 months, limits the shelflife of the entire cartridge to only six months, arguably the minimum practical shelflife for an in-vitro diagnostic product. On the other hand, 14 months is clearly an acceptable shelflife.

Other factors which discourage use of PP-lined laminates are their greater stiffness and higher melting points. PP durometer hardness, on the Shore D scale (ASTM Designation: D 2240-91 American Society for Testing and Materials, Philadelphia, Pa.), is 70–80 compared with only 44–48 for PE. Stiffness impedes high surface:volume ratio, which improves shelflife, and makes automation on form/fill/seal machines more difficult. The higher melting point for PP, 171° C. compared to only 137.5° C. for PE, requires more energy, time, or both to seal the bags.

Other variations in the packaging method are possible. For example, other shapes of packages that reduce the ratio of surface area of package to volume of solution and gas within the package (e.g., 2 circular pieces of film which are sealed together), would reduce even further the exposure of the solution and gas to the film, even further reducing the oxygen degradation. The packaging disclosed herein is also effective in protecting tonometered solutions containing other gases aside from oxygen. Furthermore, various configurations of package (e.g., three-sided seal or side-seam; four-sided sealed; gusseted packages; or "stand-up" pouches) can be used. (Compare, for example, FIG. 1c, which shows 4 sides sealed, to FIG. 1d, which shows a 3-sided seal.) These package variations affect utility of the packaging method and are not simply design alternatives. Other variations will be apparent to those with expertise in this technology area.

The Access Device

The access device is attached inside of the package. Attachment can be achieved using any technique available, for example, via use of adhesive, heat-bonding, ultrasonic welding, etc. This access device is an optional component of the package and is particularly useful when the contents of the container are used over a period of time after a prolonged storage interval. In previous approaches, a valve has been sealed into the edge or through the wall of the container so that it would be accessible from the outside of the container. However, in the package used herein, the access device is sealed totally within the package on the inner wall, and does not breach the seal or the walls of the container.

Figure 1C:
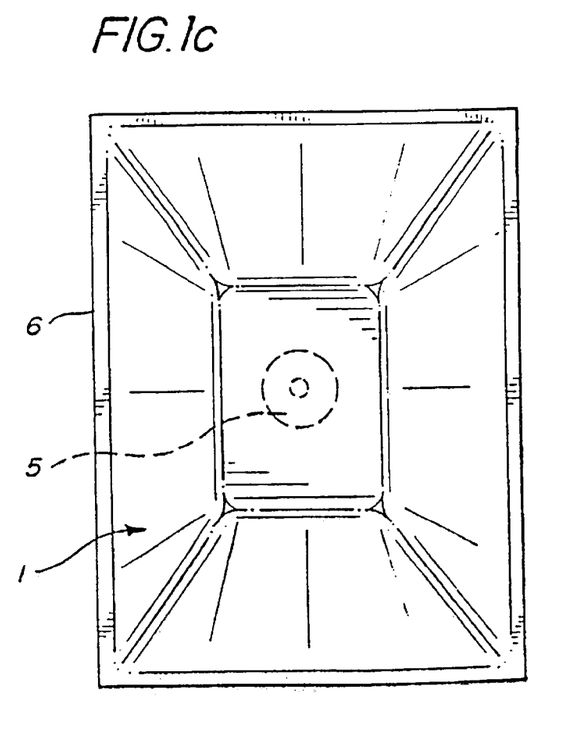
Figure 1D:
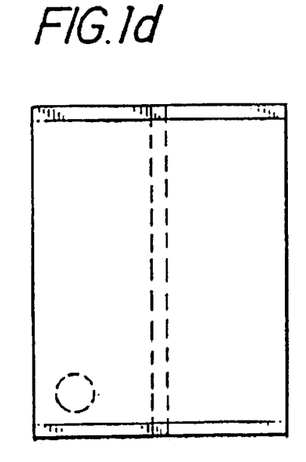
FIG. 1d is a frontal view of a three-sided, center seam package.
Figure 2:
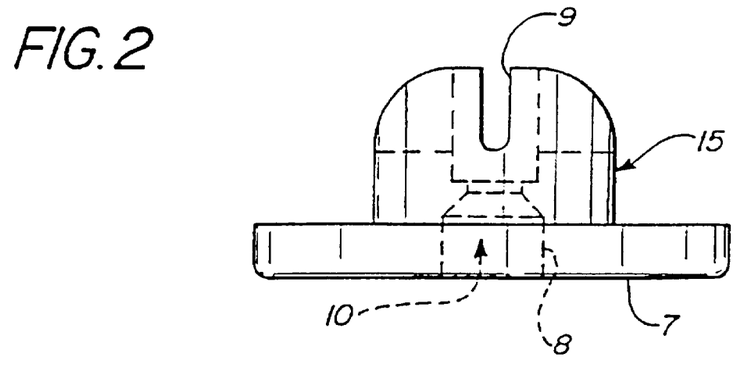
FIG. 2 is a side view of an access device used in the methods of this invention.
Figure 3:
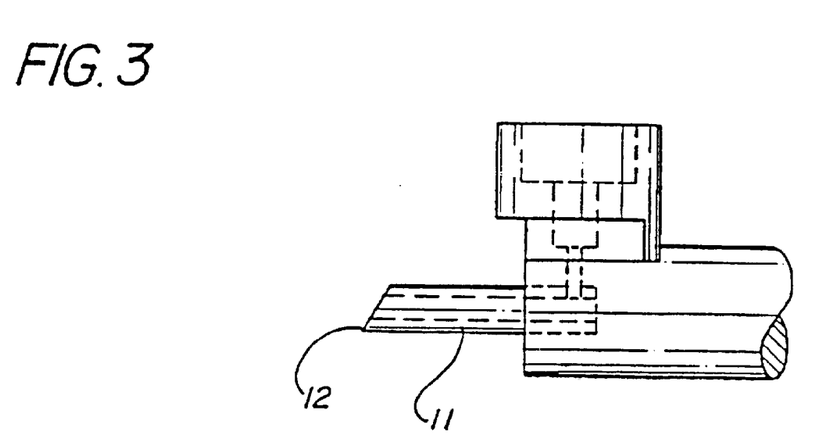
FIG. 3 is a side view of a probe which pierces the foil laminate and fits into the access device of FIG. 2.
Figure 4A:
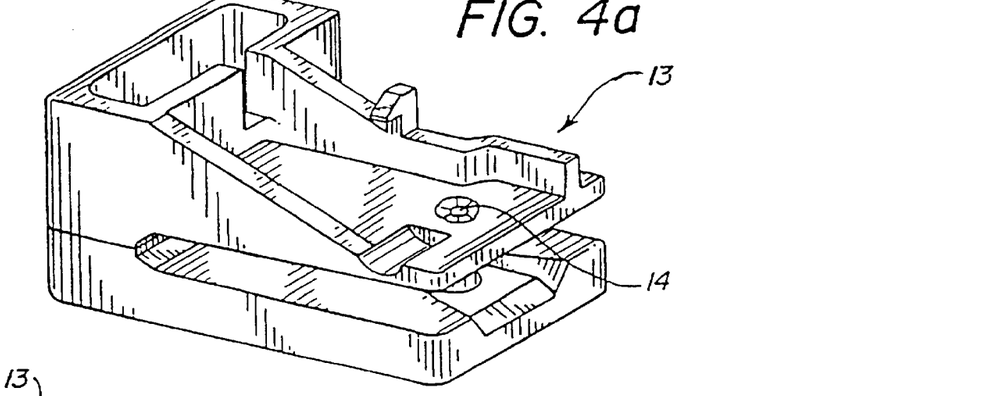
FIG. 4a is a diagram of a clamp and locating device that can be used in conjunction with the foil laminate containers of this invention.
Figure 4B:
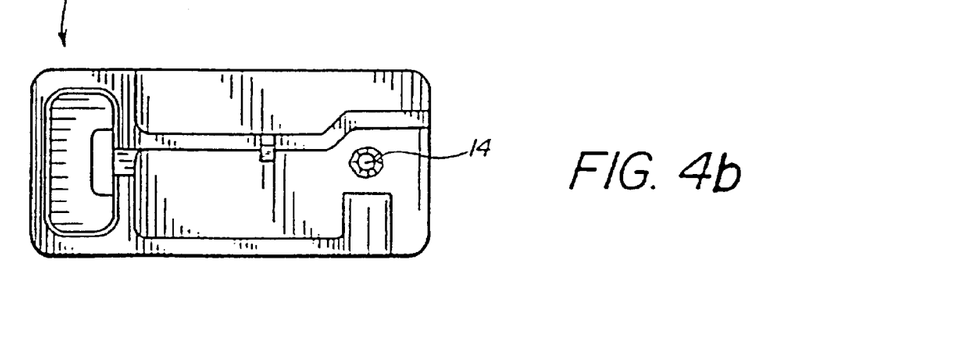
Figure 4C:
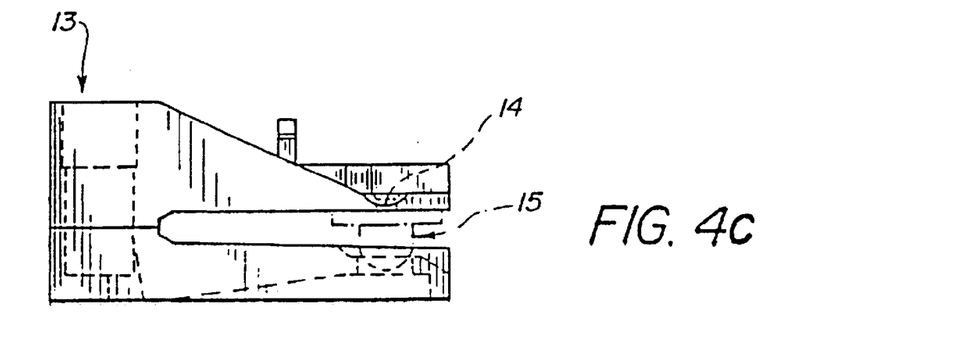

FIGS. 1a, 1c and 1d show typical locations for the access device. FIG. 2 shows the detail of a typical access device, with 7 being the portion of the access device sealed to the wall of the container, 8 being the outer portion of the delivery channel, 9 being the inner portion of the delivery channel, and 10 being the sealed portion of the delivery channel which is punctured by the probe, which then makes a tight fit with the inner portion of the delivery channel, thus preventing leakage from the container. FIG. 3 shows a typical probe, which is used to puncture the bag and fit into the access device inside the bag, with 11 representing the probe and 12 representing the sharp end of the probe which punctures the sealed portion of the delivery channel. The probe is incorporated in a clamping device 13 (see FIG. 4a, 4b and 4c) which has a circular opening 14 which fits over the hemispherical back of the access device 15 aligning the probe with the delivery channel. The probe is connected to other components which allow the oxygen reference solution to flow to the apparatus where it can be utilized in assays. When the package is punctured, the probe pierces the wall and forms a tight seal with the delivery channel of the access device. Before the package is punctured, the access device is totally isolated within the (more or less) impermeable walls of the container. This approach has an advantage over other valves and access devices in that it does not provide a diffusion pathway to the outside environment. obviously there can be variations in the design of the access device and probe, which will be apparent to those with skill in the art.

The access device is also made of PP so that it seals well with the wall of the container. The description of the access device should allow for some variations of the preferred access device. For example, the access device might be sealed to both walls of the package to provide an added benefit of stabilizing the shape of the package. The access device can be sealed at any location inside the container, for example, in a corner (for ease of attaching a clamp) or away from the edge of the container. Furthermore, the access device does not need to be attached to the container if there is some technique incorporated for locating the access device. For example, if the access device were to contain an embedded magnet, the application of an exterior magnet could be used to capture and position the access device. Other shapes (cones, indents, etc.) might be used for the locating feature. Rings can be molded into the inner wall of the delivery channel to improve the seal after puncture. The travel distance of the probe can be limited to prevent puncture of the adjacent wall of the container.

Tubing

The access device of the packaging of this invention extends the use life of oxygen reference solutions. Once the packaging is opened, the access device is designed to minimize oxygen diffusion thereby increasing the use life of the reference solution. Further, flexible and relatively gas impervious tubing is used to minimize oxygen diffusion.

The tubing conveys the oxygen reference solution from the package through the pierce probe (FIG. 3) to the analyzer. For example, in FIG. 3, such tubing would have a diameter which fits tightly into the second of the three cylindrical regions, wherein the third cylindrical region has the same diameter as the internal diameter of the tubing (illustrated with broken lines in FIG. 3) that intersect the pierce probe (11).

It is preferred that the durometer (Shore D scale) of such tubing be in a range of from 10 to 100, preferably from 70 to 94, and more preferably from 80 to 84. Condensation polymers having the requisite durometer characteristics are preferred, particularly preferred are polyamide condensation polymers, more preferred are polyester/polyether block co-polymers or polyester elastomers. Especially preferred tubing is Nylon™ [DuPont; Wilmington, Del. (USA)] and Hytrel™ 8238 [DuPont].

Representative experiments below are described wherein tubing materials can be tested for suitability for use in the methods of this invention. Silicone, fluoropolymers and plasticized polyvinylchloride were thereby determined not to be suitable tubing materials.

Use Life—Selecting Tubing Material

Similar to shelf life, which is often limited by $pO_2$ due to reaction of oxygen with packaging or contents, use life is also often limited by $pO_2$, but by a different mechanism—diffusion. The effectiveness of the access device design of the foil laminate packaging of this invention minimizes $pO_2$ diffusion. This study employed two flexible tubing materials—Hytrel 6356 [DuPont] and Zytel 42 Nylon [DuPont]. That tubing was used to conduct the oxygen reference solution from the probe of FIG. 3 (as discussed above) which fits into the access device of the foil laminate pouch to the analyzer (M288 model from CDC, supra).

An open bag use life test was run on the following formulation which had a $pO_2$ of 40 mmHg:

| | |
|---|---|
| $NaHCO_3$ | 20 mmol/L |
| NaCl | 65 |
| KCL | 3.2 |
| $CaCl_2$ | 2.8 |
| Citric Acid | 1.7 |
| LiCl | 6 |
| MOPS | 40 |
| Brij 700 | 0.05 g/L |
| Cosmocil CQ | 0.10. |

Figure 6:
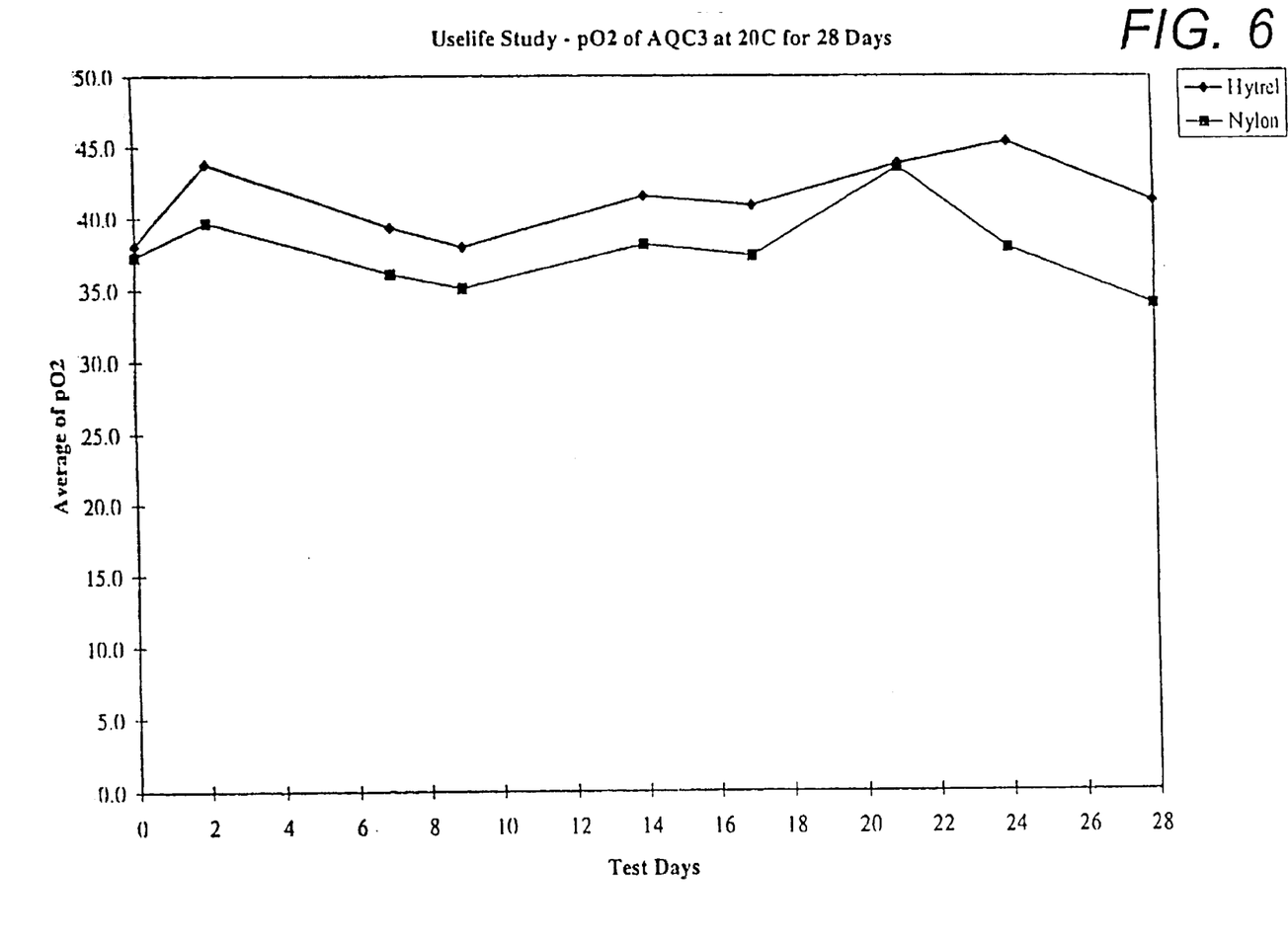
FIG. 6 graphically demonstrates a use life study wherein $pO_2$ of a representative automated quality control formulation over time was measured, wherein the tubing used to convey solutions from the pierce probe to the fluidic selection valve of the foil laminate pouch was either Nylon™ [DuPont; Wilmington, Del., USA] or Hytrel™ 6356 [Dupont].

The $pO_2$ equilibrium point is approximately 190 mmHg at 22° C. when measured at 37° C. The lower $pO_2$ within the bag increases the driving force for oxygen from room air to diffuse into the bag and thereby into the test solution. Six bags were tested over a 28-day period using 2 M288s [CDC, supra]. Results are summarized in the table below and in FIG. 6.

TABLE 15

Use Life Test of Very Low $pO_2$ Solutions in Bags with Nylon v. Hytrel Tubing

| | Change if $pO_2$ over 28 days | |
|---|---|---|
| | Hytrel 6356 | Zytel 42 Nylon |
| Bag 1 | +3.5 mmHg | −0.9 mmHg |
| Bag 2 | +0.7 | −1.3 |
| Bag 3 | +3.0 | +2.1 |
| Mean | +2.4 | ±0.0 |

A reasonable tolerance limit for allowable $pO_2$ change is ±4 mmHg at this low $pO_2$. It can be seen that all six bags performed within this range, but the bags with Nylon tubing attached had, on average, less increase in $pO_2$ over the test period.

The inventors' best explanation for the greater stability of $pO_2$ in the bags with Nylon tubing attached is that the Nylon has a higher durometer, or hardness, than the Hytrel 6356. Using the Shore D scale (ASTM Designation, supra), Zytel 42 Nylon (Dupont) is rated 82 compared with 63 for Hytrel 6356. The higher durometer implies that the molecules of the nylon are packed more tightly together both making the material more rigid and making it more difficult for gas molecules to diffuse through the interstitial spaces. Therefore, Zytel 42 Nylon, and presumably other nylons are preferred tubing materials. Also, Hytrel 8238 has the requisite durometer and is a preferred tubing material.

Further experiments with tubing materials were performed, wherein aqueous solutions were tonometered with a gas mixture containing no oxygen, aspirated into a section of test tubing sufficient to contain 100 µL using a syringe, held in the tubing for 60 seconds, and then aspirated into a model 288 analyzer [CDC, supra] beyond the segmentation valve by manually turning the pump roller. The resulting $pO_2$ readings served as indicators of the degree to which oxygen from the tubing diffused into the aqueous solutions. More than 15 tubing materials were tested in this manner. The results indicated that polyester/polyether block co-polymers, notably Zytel 42 Nylon and Hytrel 8238, are preferred tubing materials. Another preferred tubing material is Saran™ [polyvinylidene chloride; Dow Chemical Company; Midland, Mich. (USA)]. Silicone, fluoropolymers and plasticized polyvinylchloride were found not to be suitable as tubing materials.

Reactivity of Oxygen with Polypropylene

Oxygen is much less reactive with PP than it is with polyethylene. It is this lower reactivity that makes PP a more desirable material to be used as an inner layer of the foil laminate packaging of this invention. In the past, developers were concerned with permeability of the inner layer to oxygen, but this turns out, however, to be a less important attribute than the reactivity for this type of reference solution.

Both PP and PE provide reasonable sealing, although the PP has a higher melting temperature. In addition, both materials provide equivalent protection against liquid leakage. However, in polyethylene, there is more reactivity between oxygen and the polymer, thus reducing the oxygen level. It is not permeation through the polyethylene film that was largely responsible for reducing the oxygen level. This argument is based on the following numbered points.

1. Although the $pO_2$ level in the oxygen reference solution seems to be considerable, at roughly 200 mmHg, in molar terms, it is only 0.27 mmol/L. The calculation to convert from mm Hg partial pressure to mmol/L oxygen concentration is reasonably simple and straightforward, but oxygen is rarely described in the literature in molar units. Rather, where it is not in partial pressure units such as mm Hg or kPa, it is found in concentration units such as mg/L or mL/dL. However, approaching the oxygen loss problem from the molar perspective teaches us that reaction of only 0.005 mmol/L (2%) would cause product failure. Ultraviolet (UV) spectroscopy studies showed that at elevated temperatures, water-soluble, UV-absorbing substances are extracted from the sealing layer into the bag contents. This is true for both PP- and PE-lined bags. Finally, whereas only 0.005 mmol/L reactant is required for product failure (by $pO_2$ decrease), with 100 mL reagent in a 4"×6" bag, only 0.1% of an additive with a molecular weight of 500 in a 4 mil PP film would provide 0.05 mmol/L of oxidizable reactant, ten times the amount needed to explain a 2% decline in $pO_2$. Thus, the stoichiometry is reasonable, even assuming an extraction efficiency of only 10%.

2. PP sealing layers from different vendors differ markedly in the $pO_2$ changes in oxygen calibrator sealed within them when they are subjected to elevated temperatures, as demonstrated in Table 11 above. Yet the permeability of polypropylene roll stock from any of the several vendors can be expected to be similar because it should be a property of the bulk polymer, unless it has been modified into an oriented polypropylene. (Oriented PP is not known to be laminated to aluminum foil.) Thus, it is unlikely that permeability differences can explain the differences in $pO_2$ deltas shown in Table 11. However, since the various PP vendors are known to use a considerable variety of additives to the basic PP resin (these additives being nearly always proprietary), it is quite likely that differences in additives among the various resins explain a considerable portion of the differences in $pO_2$ deltas, as different additives or even the same additives in different concentrations would react to a greater or lesser degree with the oxygen in the calibrator.

3. The most convincing evidence to support the importance of reactivity over permeability is from an experiment which isolated the two effects. A uniform population of 3-side-sealed PP-lined bags were filled with an oxygen calibration solution tonometered such that oxygen partial pressure would be roughly 200 mmHg. A control group of the same bags was filled normally and immediately sealed on the Toss impulse sealer. Two test groups had five pieces, cut so as to just fit into the bag, of either polyethylene or polypropylene added to the bags just before filling and sealing. As in the stability tests described above, some bags from all three groups were left at room temperature, while others, randomly selected, were stored at 55° C. for 1, 2, and 3 weeks. Bags were cooled to and allowed to equilibrate at room temperature for at least 24 hours, and then tested in the usual manner, that is, in triplicate on two 200-series blood gas analyzers [CDC, Medfield, Mass. (USA)], alternating during runs between control and test conditions. The following results were obtained:

| Test Group | Stress Condition | $pO_2$, mean (SD) | $\Delta pO_2$ | Net $\Delta pO_2$ |
|---|---|---|---|---|
| Control | Control | 201(3) mmHg | | |
| | 3 wks at 55° C. | 191(1) | −10 mmHg | |
| +Polypropylene | Control | 219(3) | | |
| | 3 wks at 55° C. | 206(6) | −13 | −3 mmHg |
| +Polyethylene | Control | 221(2) | | |
| | 3 wks at 55° C. | 179(6) | −42 | −32 |

The effect of the polyethylene on $pO_2$ is both dramatic, being an order of magnitude more severe than polypropylene, and significant, with the additional 29 mmHg decrease being nearly five times the greatest SD, 6 mmHg. Permeability cannot explain this difference because the plastic sheets were contained entirely within the bags.

The description of the foregoing embodiments of the invention have been presented for purposes of illustration and description. They are not intended to be exhaustive or to limit the invention to the precise form disclosed, and obviously many is modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated. It is intended that the scope of the invention be defined by the claims appended hereto.

All references cited herein are hereby incorporated by reference.

What is claimed is:

1. A method for maintaining a partial pressure of oxygen in a multi-analyte reference solution in a zero headspace container at a specified value ±4 mmHg at room temperature, said method comprising:

(a) providing a container formed from a multi-layer laminate comprising (i) an inner layer that has low or no oxygen reactivity,
(ii) a middle layer comprising aluminum,
(iii) an outer layer that protects the middle layer from physical damage, and
(iv) an access device that enables removal of the solution from the container's interior;

(b) filling the container with the multi-analyte reference solution; and (c) sealing the container so as to form zero headspace within the container by forming a seal at an edge of the container, thereby sealing the access device entirely within the container without breaching the multi-layer laminate and without interrupting the seal at the edge of the container.

2. The method according to claim 1 wherein said inner layer is polypropylene.

3. The method according to claim 2 wherein the partial pressure of oxygen is maintained at said specified value ±4 mmHg at room temperature for at least six months.

4. The method according to claim 2 wherein said inner layer has a thickness of approximately 1.5 mil to 5 mil, said middle layer has a thickness of approximately 0.3 mil to 1 mil and said outer layer has a thickness of approximately 0.1 to 2 mil.

5. The method according to claim 4 wherein said inner layer has a thickness of about 2 to 5 mil and said middle layer has a thickness of about 0.5 to 0.7 mil.

6. The method according to claim 5 wherein said inner layer has a thickness of about 4 mil, said middle layer has a thickness of about 0.5 mil and said outer layer is either a lacquer coating, polyester, or nylon.

7. The method according to claim 2 wherein said outer layer is polyester.

8. The method according to claim 1 wherein the specified value is between 20 mmHg and 700 mmHg and said partial pressure is maintained at said specified value ±4 mmHg at room temperature for at least six months.

9. The method according to claim 1 wherein said partial pressure of oxygen is between 20 mmHg and 700 mmHg, inclusively.

10. The method according to claim 1 wherein said partial pressure of oxygen is between 30 mmHg and 500 mmHg, inclusively.

11. The method according to claim 1 wherein said access device is connected to one or more walls of said container.

12. The method according to claim 1 wherein step (c) further comprises forming said container into a 3-side, center-sealed pouch.

13. The method according to claim 1 wherein said multi-analyte reference solution calibrates or controls for $pO_2$ and one or more other analytes selected from the group consisting of pH, $pCO_2$, electrolytes, metabolites, tHb, CO-Ox fractions and hematocrit.

14. The method according to claim 13 wherein said metabolites are selected from the group consisting of glucose, lactate, bilirubin, urea and creatinine.

15. The method according to claim 1 further comprising, before step (b), formulating said multi-analyte reference solution with chemicals selected for low or no oxygen reactivity.

16. The method according to claim 15 wherein said chemicals are organic.

17. The method according to claim 16 wherein said partial pressure of oxygen is between 20 mmHg and 700 mmHg, inclusively.

18. The method according to claim 17 wherein said partial pressure of oxygen is between 30 mmHg and 500 mmHg, inclusively.

19. A multi-analyte reference solution with stable partial pressure of oxygen in a zero headspace container, wherein said stable partial pressure of oxygen is maintained according to the method of claim 15.

20. A multi-analyte reference solution with stable partial pressure of oxygen in a zero headspace container, wherein said stable partial pressure of oxygen is maintained according to the method of claim 1.

21. The method according to claim 1 further comprising, after step (c), piercing the access device with a probe that is connected to an analyzer through tubing that has a durometer in the range of 10 to 100.

22. The method according to claim 21 wherein said tubing has a durometer in the range of 70 to 94.

23. The method according to claim 21 wherein said tubing has a durometer in the range of 80 to 84.

24. The method according to claim 21 wherein said tubing is a polyamide condensation polymer.

25. The method according to claim 21 wherein said tubing is a polyester/polyether block co-polymer or a polyester elastomer.

* * * * *